United States Patent [19]

Reed et al.

[11] Patent Number: 5,620,688
[45] Date of Patent: Apr. 15, 1997

[54] METHODS OF INHIBITING THE ACTIVATION OF FACTOR XIII

[75] Inventors: Guy L. Reed, Winchester, Mass.; Gary R. Matsueda, Princeton, N.J.; Edgar Haber, Salisbury, N.H.

[73] Assignees: Bristol-Myers Squibb Company, Princeton, N.J.; General Hospital Corporation, The, Boston, Mass.

[21] Appl. No.: 117,052

[22] PCT Filed: Mar. 11, 1992

[86] PCT No.: PCT/US92/01926

§ 371 Date: May 4, 1994

§ 102(e) Date: May 4, 1994

[87] PCT Pub. No.: WO92/15609

PCT Pub. Date: Sep. 17, 1992

Related U.S. Application Data

[63] Continuation-in-part of Ser. No. 667,296, Mar. 11, 1991, abandoned.

[51] Int. Cl.⁶ .................. A61K 39/395; A61K 38/48; A61K 38/49
[52] U.S. Cl. ................... 424/145.1; 424/130.1; 424/139.1; 424/141.1; 424/146.1; 424/156.1; 424/94.63; 424/94.64
[58] Field of Search .............. 424/130.1, 139.1, 424/141.1, 145.1, 146.1, 158.1, 94.63

[56] References Cited

U.S. PATENT DOCUMENTS 4,968,713  11/1990  Baldwin et al. ............. 514/398

FOREIGN PATENT DOCUMENTS

| | | |
|---|---|---|
| 0294016 | 12/1988 | European Pat. Off. . |
| WO89/11865 | 12/1989 | WIPO . |
| WO91/07432 | 5/1991 | WIPO . |
| WO91/17258 | 11/1991 | WIPO . |

OTHER PUBLICATIONS

Collen Lancet: 34L: 34–36(1993).

Marder N. Eng. J. Med. 318: 1512–1520 (1988).

Mann et al. in Hemostails & Thrombosis, Coleman Ed. Lippencott Phila PA pp. 112–125 1987.

Harris, Tibtech 11:42–45 (1993).

Kavanaugh et al. Arthritis & Rheumatism 37:992–999 (1994).

Coller et al. Thrombosis & Hemostasis 74(1) 302–308 (1995).

The Epics Investigators N. Eng. J. Med. 330:956–961 (1994).

Aihara, M. et al., Factor XIII is Not Involved in Human Platelet–Collagen Interaction, *Tohoku J. Exp. Med.* 159(1):37–44 (Sep. 1989).

Baja, P.S. et al., Experimental and Theoretical Evidence Supporting the Role of $Gly^{363}$ in Blood Coagulation Factor IXa ($Gly^{193}$ in Chymotrypsin) for Proper Activation of the Proenzyme, *J. Biol. Chemistry* 265(5):2956–2961 (Feb. 15, 1990).

Birkedal–Hansen, B. et al., Monoclonal Antibodies to Human Fibroblast Procollagenase. Inhibition of Enzymatic Activity, Affinity Purification of the Enzyme, and Evidence for Clustering of Epitopes in the $NH_2$–Terminal End of the Acitvated Enzyme, *Biochemistry* 27:6751–6758 (1988).

Board, P.G. et al., Expression of Functional Coagulation Factor XIII In *Escherichia coli, Thrombosis and Haemostasis* 63(2):235–240 (Apr. 12, 1990).

Bohn, H., Isolierung und Charakterisireung des fibrinstabilisierenden Faktors aus menschlichen Thrombozyten, *Thromb. Diath. Haemorrh.* (Germany, West) 23:(3):455–468 (Jun. 30, 1970).

Colasanti, G. et al., deposition of fibrin–stabilizing factor (F XIII A and S), fibrinogen–related antigens, fibrinogen degradation products (FDPd and FDPe) and antihemolytic factor (F VIII) in renal disease: analysis of 161 cases by immunofluorescence microscopy, *Clin. Nephrol.* 28(1):28–34 (1987).

Coller, B.S., Platelets and Thrombolytic Therapy, *New England Journal of Medicine* 322(1):33–42 (Jan. 4, 1990).

Davis III, A.E., C1 Inhibitor (C1 INH): Genes, Biosynthesis, and Biology, *Behring Inst. Mitt.* 84:142–150 (1989).

deFouw, N.J. et al., Activated Protein C Increases Fibrin Clot Lysis by Neutralization of Plasminogen Activator Inhibitor—No Evidence for a Cofactor Role of Protein S, *Thromb. Haemost.* 60(2):328–333 (Oct. 31, 1988).

Degen, S.J.F. et al., Characterization of the Complimentary Deoxyribonucleic Acid and Gene Coding for Human Prothrombin, *Biochemistry* 22:2087 (1985).

Doyle, P.M. et al., Peptides incorporating electrophilic glutamine analogues as potential transglutaminase inhibitors, *Biochemical Society Transaction* 18:1318–1320 (1990).

Elms, M.J. et al., Rapid Detection of Cross–Linked Fibrin Degradation Products in Plasma Using Monoclonal Antibody–Coated Latex Particles, *Am. J. Clin. Pathol.* 85(3):360–364 (mar. 1986).

(List continued on next page.)

*Primary Examiner*—Christina Y. Chan
*Assistant Examiner*—Phillip Gambel
*Attorney, Agent, or Firm*—Sterne, Kessler, Goldstein & Fox P.L.L.C.

[57] ABSTRACT

Compositions and methods for inhibiting the activation and/or active state of a precursor protein are provided. Compositions provided can bind to a cleavage site of a precursor protein. Also provided are compounds useful for generating inhibitor compositions. Application of the invention to the treatment of myocardial infarction and other thrombotic conditions is specifically provided. Further provided are antibodies specific for active Factor XIII.

8 Claims, 1 Drawing Sheet

OTHER PUBLICATIONS

Foster, D.C. et al., The nucleotide sequence of the gene for human protein C, *Proc. Natl. Acad. Sci. USA* 82:4673 (1985).

Freifelder, D., in *Molecular Biology; A Comprehensive Introduction to Prokaryotes and Eukaryotes*, Jones and Bartlett Inc., pp. 478–480 (1983).

Gaffney, P.J. et al., Fibrin Crosslinks And Lysis Rates, *Thrombosis Research* 14:85–94 (1979).

Gershenfeld, H.K. et al., Cloning of a cDNA for a T Cell–Specific Serine Protease from a Cytotoxic T Lymphocyte, *Science* 232:854–858 (May 16, 1986).

Gogstad, G.O. et al., Platelet factor XIII is an active enzyme after solubilization and crossed immunoelectrophoresis, *Thrombosis Research* 29(2):237–241 (Jan. 15, 1983).

Grundmann, U. et al., Characterization of cDNA coding for juman factor XIIIa, *Proc. Natl. Acad. Sci. USA* 83:8024–8028 (Nov. 1986).

Hada, M. et al., Covalent crosslinking of von Willebrand Factor to Fibrin, *Blood* 68(1):95–101 (Jul. 1986).

Harlow et al., *Antibodies: A Laboratory Manual*, Cold Spring Harbor Laboratory, pp. 72–77. 92–97, 128–135, 141–137 (1988).

Henderson, K.W. et al., The Mechanism of Enhanced Streptokinase–Induced Clot Lysis following In–vitro Factor–XIII Inactivation, *Brit. J. Haematol.* 17:445–453 (1969).

Hendriksson, P. et al., Identification of Intracellular Factor XIII in Human Monocytes and Macrophages, *J. Clin. Invest.* 76(2):528–534 (Aug. 1985).

Ichinose, A., et al., Amino Acid Sequence of the a Subunit of Human Factor XIII, *Biochem.* 25(22):6900–6906 (Nov. 4, 1986).

Ikematsu et al., Immunochemical studies of Human factor XIII, *J. Lab. Clin. Med.* 97(5):662–671 (May 1981).

Jansen, J.W.C.M. et al., Influence of Factor XIIIa Activity on Human Whole Blood Clot Lysis In Vitro, *Thrombosis and Haemostasis* 57(2):171–175 (Apr. 7, 1987).

Kelly, R.B. Pathways of Protein Secretion in Eukaryotes, *Science* 230:25–32 (Oct. 4, 1985).

Kiesselbach, T.H. et al., Demonstration Of Factor XIII In Human Megakaryocytes By A Fluorescent Antibody Technique, *Ann. N.Y. Acad. Sci.* 201:318–328 (1972).

Kirchheimer, J.C. et al., Matrix–Bound Plasminogen Activator Inhibitor Type 1 Inhibits The Invasion of Human Monocytes Into Interstitial Tissue, *J. Immunol.* 145(5):1518–1522 (Sep. 1, 1990).

Lerner, R.A.,, Tapping the immunological repertoire to produce antibodies of predetermined specificity, *Nature* 299:592–596 (Oct. 14, 1982).

Lopaciuk, S. et al. Differences between Type I Autoimmune Inhibitors of Fibrin Stabilization in Two Patients with Severe Hemmorhagic Disorder, *J. Clin. Invest.* 61:1196–1203 (1978).

Lorand et al., Autoimmune antibody (IgG Kansas) against the fibrin stabilizing factor (factor XIII) system, Proc. *Natl. Acad. Sci. USA* 85:232–236 (Jan. 1988).

Lukacova, D. et al., Functional Characteristics Of A Monoclonal Antibody Directed To The Thrombin Activation Site Of Faxtor XIII, *FASEB J.* 5(4):A515 (1991).

Lukacova, D. et al., Inhibition of Factor XIII Activation by an Anti–Peptide Monoclonal Antibody, *Biochem.* 30:10164–10170 (1991).

McDonagh, J. et al., Alternative Pathways for the Activation of Factor XIII, *Br. J. Haematol.* 30:465–477 (1975).

McDonagh, J. et al., Site Of Synthesis Of Plasma And Platelet Factor XIII, *Ann. N.Y. Acad. Sci.* 202:31–40 919720.

McDonagh, J., Structure and Function of Factor XIII, in *Hemostasis & Thrombosis*, 2nd Edition.

McMullen, B.A. et al., Complete Amino Acid sequence of the Light Chain of Himan Blood Coagulation Factor X: Evidence for Identification of Residue 63 as β–Hydroxyaspartic Acid, *Biochemistry* 22:2875–2884 (1983).

Muszbek, L. et al., Factor XIII Of Blood Coagulation In Human Monocytes, *Thromb, Res.* 37(3):401–410 (Feb. 1, 1985).

Human, R.L. et al., Immunological Studies of Proteins Associated with the Subcellular Fractions of Thrombasthenic an Afibrinogenaemic Platelets, *Brit. J. Haemat.* 15(2):181–189 (Aug. 1968).

Neurath, H., Evolution of Proteolytic Enzymes, *Science* 224:350–357 (Apr. 27, 1984).

Nilsson, J.L.F. et al., Fibrin–Stabilizing Factor Inhibitors, *Annals of the New York Academy of Sciences* 202:286–296 (1972).

Panis, R. et al., Risk of Hepatitis in Fibrin Adhesion, *Laryng. Rhinol. (Stuttgart)* 60(7):367–368 (Jul. 1981).

Pincus, S.E. et al., in Inouye, M. et al., *Molecular Biology of RNA*, pp. 175–180 (1987).

Procyk, R. et al., Factor XII–induced crosslinking in solutions of fibrinogen and fibronectin, *Biochim. Biophys. Acta* 967(2):304–313 (Nov. 17, 1988).

Reed, G.L. et al., Fibrin–fibrin and α2–antiplasmin–fibrin cross–linking by platelet factor XIII increases the resistance of platelet clots to fibrinolysis, *Trans. Assoc. Am. Physicians* 104:21–28 (1991).

Rinderknecht, H., et al., A possible zymogen self–destrcut mechanism preventing pancreatic autodigestion, *Int. J. Pancreatol.* 3:33–44 (1988).

Schmaier A.H. et al., Determination of the Bifunctional Properties of High Molecular Weight Kininogen by Studies with Monoclonal Antibodies Directed to Each of Its Chains, *J. Biol. Chem.* 262(3):1405–1411 (Jan. 25, 1987).

Scott, C.F. et al., A New Assay For High Molecular Weight Kininogen In Human Plasma Using A Chromogenic Substrate, *Thrombosis Research* 48:685–700 (1987).

Scott, C.F. et al., Inactivation of Factor XIa by Plasma Protease Inhibitors, *J. Clin. Invest.* 69:844–852 (Apr. 1982).

Selmayr, E. et al., Crosslinking Of Soluble Fibrin And Fibrinogen, *Thrombosis Research* 39(4):467–474 (Aug. 15, 1985).

Shebuski, R.J. et al., Acceleration of tPA0–induced Thrombolysis by an Inhibitor of Factor XIIIa in a Canine Model of Coronary Arterial Thrombosis, *Circulation* 80(Suppl):II–217, Abstract No. 0866 (1989).

Sixma, J.J. et al., Immunocytochemical Localization of Albumin and Factor XIII in Thin Cryo Sections of Human Blood Platelets, *Thrombosis and Haemostasis* 51(3):388–391 (Jul. 29, 1984).

Takahashi, N. et al., Primary structure of blood coagulation factor XIIIa (fibrinoligase, transglutaminase) from human placenta, *Proc. Natl. Acad. Sci. USA* 86:8019–8023 (1986).

Vehar, G.A. et al., Structure of human factor VIII, *Nature* 312:337–342 (1984).

Wayland, W. et al., Should an injured spleen be preserved?, *Zent.bl. Chir.* 111(5):241–251 (1986).

Yoshitake, S. et al., Nucleotide Sequence of the Gene for Human Factor IX (Antihemophillic Factor B), *Biochemistry* 24:3736–3750 (1985).

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( C ) STRANDEDNESS: unknown
        ( D ) TOPOLOGY: unknown ( i i ) MOLECULE TYPE: peptide ( i x ) SEQUENCE DESCRIPTION: SEQ ID NO:1:

Gly Val Asn Leu Gln Glu Phe Cys
    1                    5

( 2 ) INFORMATION FOR SEQ ID NO:2:

( i ) SEQUENCE CHARACTERISTICS:
        ( A ) LENGTH: 8 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:2:

Pro Arg Gly Val Asn Glu Gln Phe
    1                    5

( 2 ) INFORMATION FOR SEQ ID NO:3:

( i ) SEQUENCE CHARACTERISTICS:
        ( A ) LENGTH: 8 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:3:

Gly Val Asn Leu Gln Glu Phe Cys
    1                    5

( 2 ) INFORMATION FOR SEQ ID NO:4:

( i ) SEQUENCE CHARACTERISTICS:
        ( A ) LENGTH: 10 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:4:

```
       Pro Arg Gly Val Asn Leu Gln Glu Phe Cys
       1               5                   10
```

( 2 ) INFORMATION FOR SEQ ID NO:5:

( i ) SEQUENCE CHARACTERISTICS:
        ( A ) LENGTH: 8 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:5:

```
       Gly Val Asn Leu Arg Glu Phe Cys
       1               5
```

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:6:

```
       Pro Arg Gly Val Asn Leu Gln Glu Phe
       1               5
```

( 2 ) INFORMATION FOR SEQ ID NO:7:

( i ) SEQUENCE CHARACTERISTICS:
        ( A ) LENGTH: 9 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:7:

```
       Pro Arg Gly Val Asn Leu Gln Glu Phe
       1               5
```

( 2 ) INFORMATION FOR SEQ ID NO:8:

( i ) SEQUENCE CHARACTERISTICS:
        ( A ) LENGTH: 9 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:8:

```
       Pro Arg Gly Val Asn Leu Gln Glu Phe
       1               5
```

METHODS OF INHIBITING THE ACTIVATION OF FACTOR XIII

This application is a Continuation-in-Part of U.S. application Ser. No. 07/667,296, filed Mar. 11, 1991, now abandoned which disclosure is herein incorporated in its entirety.

FIELD OF THE INVENTION

The present invention relates to a treatment for myocardial infarction, deep venous thrombosis, pulmonary emboli, cerebrovascular thrombosis or any thrombotic process within a patient. The present invention also relates more generally to the inhibition of any protein which exists in a precursor form (e.g., zymogen) that must be activated via proteolytic cleavage. The invention further relates to a method for the detection of an activated form of Factor XIII.

BACKGROUND OF THE INVENTION

The initiating event of many myocardial infarctions (heart attacks) is the hemorrhage into atherosclerotic plaque. Such hemorrhage often results in the formation of a thrombus (or blood clot) in the coronary artery which supplies the infarct zone (i.e., an area of coagulation necrosis which results from an obstruction of blood circulation). This thrombus is composed of a combination of fibrin and blood platelets. The formation of a fibrin-platelet clot has serious clinical ramifications. The degree and duration of the occlusion caused by the fibrin-platelet clot determines the mass of the infarct zone and the extent of damage.

The primary goal of current treatment for myocardial infarction involves the rapid dissolution of the occluding thrombus and the restoration of blood flow ("reperfusion"). A successful therapy must be capable of sustained effect so that reformation of the clot does not occur after the cessation of therapy. If the fibrin-platelet clot is able to reform, then the affected artery may become reoccluded.

The formation of fibrin-platelet clots in other parts of the circulatory system may be partially prevented through the use of anticoagulants (such as heparin). Unfortunately, heparin has not been found to be universally effective in preventing reocclusion in myocardial infarction victims in which the degree of blood vessel occlusion (the degree of "stenosis") is greater than or equal to 70%, particularly in those patients with severe residual coronary stenosis.

If an individual has formed a fibrin-platelet clot prior to the availability of medical assistance, the clot may be dissolved through the use of thrombolytic agents. A thrombolytic agent is a medicament capable of lysing the fibrin-platelet thrombus, and thereby permitting blood to again flow through the affected blood vessel. Such agents include streptokinase, prourokinase, urokinase, and tissue-type plasminogen activator (Ganz, W. et al., *J. Amer. Coll. Cardiol.* 1:1247–1253 (1983); Rentrop, K. P. et al., *Amer. J. Cardiol.* 54:29E–31E (1984); Gold, H. K. et al., *Amer. J. Cardiol.* 53:122C–125C (1984)).

Treatment with thrombolytic agents can often successfully restore coronary blood flow rapidly enough to interrupt myocardial infarction. Unfortunately, the dissolved fibrin-platelet clot has been found to reform after cessation of such thrombolytic therapy in a substantial number of patients. This reformation may result in the reocclusion of the affected blood vessels, and is, therefore, of substantial concern (Gold, H. K. et al., *Amer. J. Cardiol.* 53:122C–125C (1984); Gold, H. K. et al., *Circulation* 68:I-50–I-54 (1983)). Thus, although streptokinase treatment has been found to be successful in dissolving fibrin clots in approximately 85% of studied cases, reocclusion of the affected vessels has been found to occur in approximately 25% of the patients examined. (Gold, H. K., et al., *Circulation* 68:I50–I54 (1983)).

Tissue-type plasminogen activator (t-PA) is considered to be a more desirable thrombolytic agent than either streptokinase or urokinase because it displays greater (though not absolute) specificity for fibrin than does either of these agents (Verstrate, M., et al., *Lancet* 1:142 (1985)). Tissue-type plasminogen activator (t-PA) is a clot-specific thrombolytic agent with a rapid disposition rate from plasma. Tissue-type plasminogen activator (t-PA) has been found to be an effective thrombolytic agent in patients with acute myocardial infarction, producing coronary reflow (i.e., decreasing stenosis) in 45–75 minutes in approximately 70% of patients studied (Gold, H. K. et al., *Circulation* 73:347–352 (1986)).

The benefit of employing t-PA is significantly offset by the spontaneous rate of acute reocclusion which follows the cessation of t-PA therapy. Gold, H. K. and coworkers have found that cessation of t-PA therapy resulted in reocclusion of affected blood vessels in approximately 45% of patients studied (*Circulation* 73:347–352 (1986)). Increased t-PA dosages have not been found to decrease the tendency for coronary artery reocclusion. Significantly, the possibility of thrombin clot reformation is closely related to the degree of residual coronary stenosis (i.e., the extent of blood vessel blockage). Thus, reocclusion is more probable in individuals in which high grade stenosis (i.e., greater than 70% quantitative stenosis or greater than 80% non-quantitative stenosis) has occurred. The reocclusion of blood vessels has been found to be inhibited by continued infusion of t-PA (Gold, H. K. et al., *Circulation* 73:347–352 (1986)). Unfortunately, the relatively short biological half-life of t-PA and the potential for increasing the tendency for severe bleeding in some patients may make continued infusion of t-PA impractical for many heart attack victims.

In summary, clinical investigations have shown that the dissolved thrombus frequently reforms following the cessation of t-PA infusion (Gold, H. K. et al., *Circulation* 73:347–352 (1986)), but that the frequency of such reocclusion can be minimized by providing a second ("maintenance") t-PA infusion of a substantially lower dose but for a substantially longer period. Heparin is currently recognized as the appropriate concomitant therapy for patients receiving such a maintenance infusion. The treatment of coronary artery thrombosis (clotting) with t-PA requires, therefore, a continuous infusion at a high rate in order to obtain rapid reperfusion, and a maintenance infusion at a lower dose to prevent reocclusion in patients with high grade residual stenosis.

Clots are composed of both fibrin and blood platelets in various ratios. The fundamental reaction in blood clotting involves the conversion of a soluble plasma protein (fibrinogen) into insoluble fibrin. The conversion of fibrinogen into fibrin is catalyzed by the enzyme, thrombin, which is a serine protease. Fibrin molecules are then extensively crosslinked by Factor XIII to other fibrin molecules via their gamma and alpha chains. In addition, α-antiplasmin is crosslinked by Factor XIII to fibrin. Both of these crosslinking events result in a clot which is highly resistant to thrombolysis. The general mechanism of blood clot formation is reviewed by Ganong, W. F. (In: *Review of Medical Physiology*, 9th ed., Lange, Los Altos, Calif., pp. 411–414 (1979)). Platelets are disk-shaped structures present in blood which contribute to clot formation by both their incorporation along with fibrin into an insoluble mass and by providing additional Factor XIII, fibrin and α2-antiplasmin their enhancement of the rate of fibrinogen to fibrin conversion. Platelets contribute to clot formation in myocardial infarction and are a major component of clots that reocclude coronary arteries that have been reperfused by treatment with a thrombolytic agent.

Factor XIII, (fibrin stabilizing factor) in its active form, is responsible for the cross-linking of fibrin monomers in the final stages of the blood coagulation cascade. Factor XIII also crosslinks α2-antiplasmin to fibrin in plasma clots and thereby makes clots resistant to plasmin and plasminogen activators. The cross-linking of fibrin and cross-linking between fibrin, fibronectin and collagen appears to play a significant part in stabilizing the clot and promoting wound healing. Mosher et al. *J. Biol. Chem.* 255:1181–1188 (1980). Plasma factor XIII is a tetramer composed of two A subunits linked as a dimer and two loosely associated B subunits. Schwartz et al. *J. Biol. Chem.* 284:1395–1407 (1973). Plasma factor XIII crosslinks fibrin by introducing γ-glutamyl-ε-lysyl bonds between the γ-chains of neighboring units in the fibrin polymer and also between the chains of these subunits. Chen et al. *Proc. Natl. Acad Sci. USA* 66:472–479 (1970).

The A and B subunits of Factor XIII have been cloned and sequenced. Ichinose et al. *Biochemistry* 25:6900–6906 (1986); Gundman et al. *Proc. Natl. Acad. Sci USA* 83:8024–8028 (1986); and Ichinose et al. *Biochemistry* 25:4633–4638 (1986).

During coagulation the A subunit zymogen of Factor XIII is activated by the thrombin catalyzed cleavage of an amino terminal peptide (4 kDa). The activated A subunit catalyzes the formation of the peptide bonds between substrate polypeptides. The B subunit has no known catalytic activity and is known to protect the A subunit from rapid degradation.

Factor XIII is a proenzyme in the coagulation system which is located in plasmin, platelets and certain tissues. When activated in the terminal phase of coagulation, it functions as a transglutaminase in the terminal phase of coagulation and chemically crosslinks fibrin. Factor XIII activity is essential for normal hemostasis, and it also appears to play a critical role in thrombosis and in wound healing.

Clot lysis is mediated by plasmin in vivo. Under natural conditions, plasminogen is converted to plasmin by tissue plasminogen activator (t-PA). Activation occurs on the fibrin surface, thus confining proteolytic activity to the appropriate site. After plasmin is set free into the circulation, it is rapidly combined with natural inhibitors. Inactivation of plasmin is the final and necessary step in the process of protecting against undesirable proteolysis. Such plasmin inhibitors include α-2-antiplasmin, α-2-macroglobulin and α-1-antitrypsin, all glycoproteins. α-2-antiplasmin has a much higher affinity for plasmin than α-2-macroglobulin and binds specifically to plasmin in a 1:1 ratio. The larger pool of α-macroglobulin acts as a reservoir inhibitor. Kane, K. K., *Ann. Clin. Lab. Sci.* 14:443–449 (1984). Thus, clot lysis by the administration of t-PA is limited by the rapid and irreversible inactivation of plasmin by plasmin inhibitors.

All available thrombolytic agents still suffer significant shortcomings, including the need for large doses to be therapeutically efficient, a limited fibrin-specificity, residual toxicity in terms of bleeding complications by the fact that they may paradoxically activate platelets and increase clotting. Cardiovascular disease is still a major cause of disability. All current agents are associated with thrombotic reocclusion of blood vessels during or after therapy. Thus, there remains a need for additional agents which can be utilized alone or in combination with known thrombolytic agents. Improvements in thrombolytic therapy which enhance clot lysis, while minimizing fibrinogen breakdown and preventing reocclusion of the affected coronary artery are needed.

SUMMARY OF THE INVENTION

One aspect of the present invention provides compositions which may be used to inhibit the activation of a precursor protein and/or its active form. These inhibitory compositions bind to a site on a precursor protein which is cleaved during activation.

Methods for using these compositions to inhibit or detect precursor proteins in vivo and in vitro are also provided.

The invention further provides peptide antigens which are capable of eliciting monoclonal antibodies which act as inhibitory compositions.

The invention is useful for the treatment of myocardial infarction and blood clots within a patient.

The invention additionally provides a method for the detection of an activated form of Factor XIII.

DETAILED DESCRIPTION OF THE INVENTION

Figure 1:
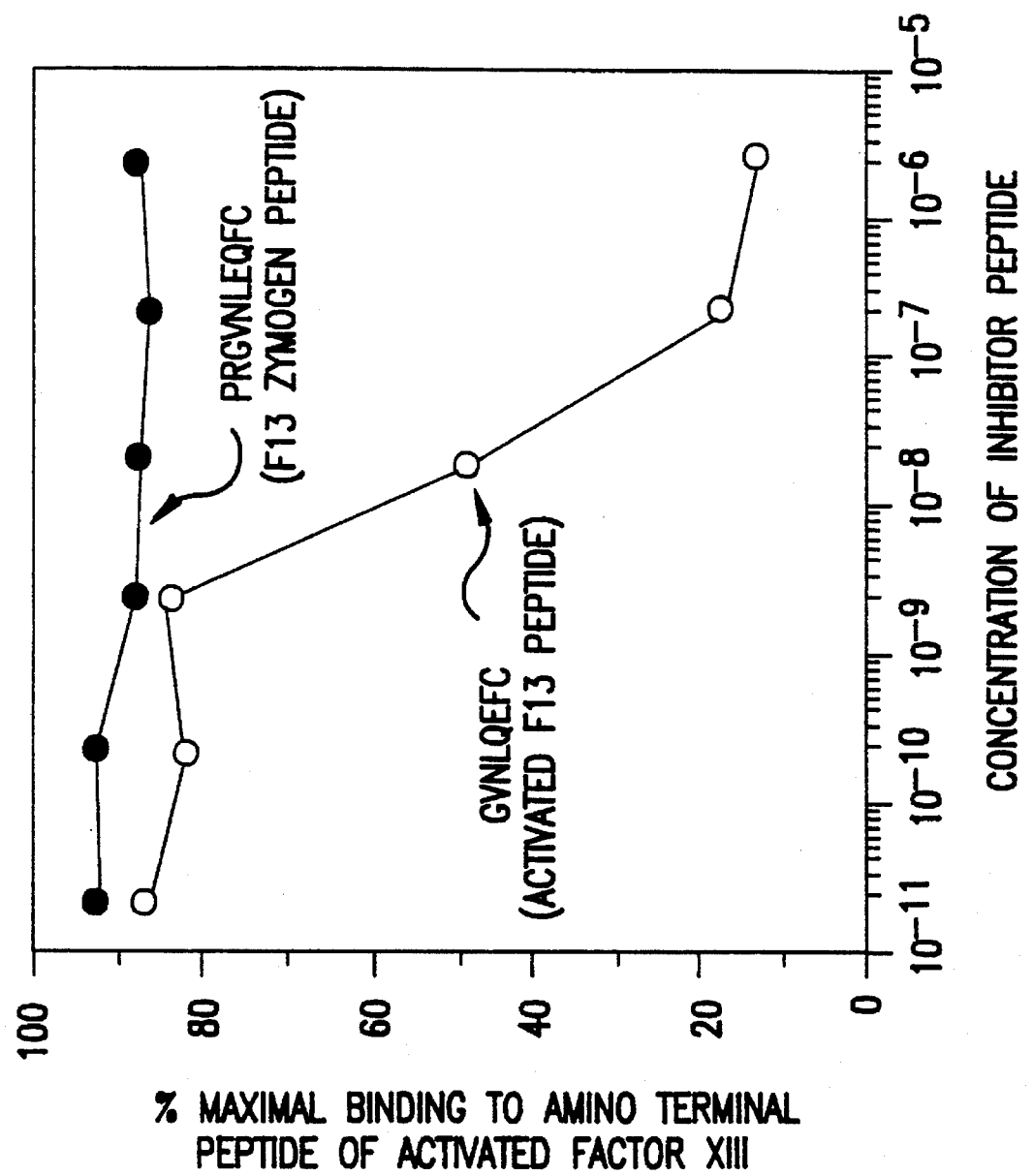
FIG. 1 is a graph representing the binding specificity of a monoclonal antibody specific for an active form of Factor XIII.

One aspect of the invention provides a unique means for inhibiting the activation and/or active state of a precursor protein. This means involves the use of novel compositions capable of binding to the cleavage site of a precursor protein.

The term "precursor protein" is used herein to describe any protein which is cleaved in vivo by normal cellular processes into two or more proteins, at least one of which possesses a particular biological activity. Cleavage products of precursor proteins may also include one or more peptides which have no discernible activity or function once they are cleaved. Precursor proteins themselves may be either biologically active or inactive.

A cleavage product of a precursor protein which possesses a particular biological activity is referred to herein as a mature or active protein or an active form of the precursor protein.

Precursor proteins may be cleaved into one or more mature proteins. Precursor proteins containing a single mature protein are typically known by the same name as that mature protein.

Examples of precursor proteins include, but are not limited to, zymogens, secretory proteins, and fused proteins derived from polycistronic mRNAs, receptors that require proteolytic cleavage for signal generation (e.g., the thrombin receptor).

A zymogen is an enzyme precursor protein made up of an activation peptide attached to a mature protein. Proteins containing the activation peptide are largely inactive. Upon cleavage of the activation peptide the mature protein is activated. Specific examples of zymogens include human coagulation Factors VII, IX, X, XI, XII, XIII, prothrombin, protein C, trypsinogen, chymotrypsin, etc. Other precursor proteins include those proteins which require enzyme cleavage to be active such as hormones or agents (e.g., atrial natriuretic peptide, endothelin), active receptors (e.g., the thrombin receptor) or coagulation proteins (e.g., fibrinogen).

Like zymogens, secretory proteins of the type described here also contain amino terminal peptides in their precursor protein state which are cleaved off to generate mature proteins. However, the amino terminal peptides of secretory proteins, known as signal peptides, facilitate the transport/secretion of the mature protein. If the signal peptide is not cleaved it may result in impaired function of the protein (e.g., as has been reported with antibodies).

Translation products of polycistronic mRNAs represent a third type of precursor protein. This type is made up of two or more mature proteins fused at the ends as a result of the translation process. Cleavage of these precursor proteins after translation releases the individual mature proteins. Many prokaryotic and viral proteins are produced from polycistronic mRNAs in this way (see Freifelder, D., *Molecular Biology; A Comprehensive Introduction to Prokaryotes and Eukaryotes*, pp.478–480, ed. by Jones and Bartlett, Inc. (1983); Pincus, S. E. et al., in *Molecular Biology of RNA*, pp175–180, ed. by M. Inouye and B. S. Dudock (1987)). Specific examples of this class of precursor proteins include poliovirus polyprotein, etc.

Activation of a precursor protein is referred to herein to denote its cleavage into component parts, including at least one active protein. The region of the precursor protein which is cleaved, including the actual site of cleavage and adjacent amino acid sequences on either side, is referred to herein as the cleavage site. Precursor proteins may have one or more cleavage site(s).

The invention provides compositions which can bind at or near the cleavage site of a precursor protein. That is, the composition can bind to the cleavage site, on the amino or carboxy terminal side of the cleavage site, or even to an amino acid in close spatial proximity to the activation site, etc. These compositions are also referred to herein as inhibitors, inhibitor compositions, and inhibitory compositions. These compositions include, but are not limited to, polyclonal antibodies, monoclonal antibodies, antibody fragments (including Fab, etc.), single chain antibodies, etc. Such inhibitors could also be composed of amino acid sequences that mimic the sequence of the cleavage site of the target protein and act as alternate inhibitory substrates for the activating enzyme.

Binding of an inhibitor composition to a precursor protein may block enzyme access to a cleavage site. In so doing this blockage may reduce cleavage of a precursor protein and account, at least in part, for the inhibitory effect of the compositions of the invention. However, it is recognized that other mechanisms may be responsible for this inhibitory effect and that the invention is not limited to any particular mechanism.

The inhibitory compositions of the invention may also interfere directly with the mature form(s) of a precursor protein. This interference could potentially occur as a result of binding of an inhibitor composition to amino acid sequences of a cleavage site that are retained by the mature form(s) of the precursor protein. However, as previously noted, other mechanisms of inhibition are also possible.

The invention further provides peptides useful for obtaining or generating inhibitor compositions of the invention. These peptides act as antigens to elicit antibodies that are inhibitor compositions of the invention and are referred to herein as peptide antigens.

Peptide antigens correspond to sites at or near the cleavage site of a precursor protein, as discussed above. Preferably, amino acid sequences of the cleavage site which are retained in the mature protein for which inhibition is desired are included.

Any length of peptide which mimics the cleavage or other site may be used as a peptide antigen to elicit antibodies which are inhibitor compositions of the invention. Generally, these peptide antigens comprise about 6 to about 20 amino acids, more generally about 8 to about 10 amino acids.

Peptide antigens of the invention may be obtained directly from the precursor or mature protein using standard protein isolation and fractionation procedures well known to those of ordinary skill in the art.

Alternatively, peptide antigens of the invention can be synthesized by the well known solid phase peptide synthesis described by Merrifield, *J. Am. Chem. Soc.* 85:2149 (1962) and Stewart and Young in *Solid Phase Peptides Synthesis* (Freeman, San Francisco, 1969) pp. 27–62, using a copoly-(styrene-divinylbenzene) containing 0.1–1.0 mMolamines/g polymer. On completion of chemical synthesis, the peptides can be deprotected and cleaved from the polymer by treatment with liquid HF-10% anisole for about ¼-I hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of the appropriate fractions of the column will yield the homogeneous peptide or their derivatives, which are then characterized by amino acid analysis, thin layer chromatography, high performance liquid chromatography, ultraviolet absorption spectroscopy, molar rotation, solubility, and quantitated by the solid-phase Edman degradation (Matsueda, G. R., Haber, E. and Margolies, M. N., *Biochemistry* 20:2571 (1981)).

The technique of synthesis and isolation is fully described in the aforementioned references, as well as in U.S. Pat. No. 4,269,827, which is herein incorporated by reference. It is to be noted that during or after the synthesis, cysteines may preferably be blocked by 3,4-dimethylbenzyl (DMB), arginines and histidines by tosyl (TOS), aspartic acid and glutamic acids by benzyl (Bzl), and lysines by 2-chlorobenzyloxycarboxyl (2-CBZ). Other protective blocking groups are well known, and can be used in the present invention.

For synthetic peptide antigens any one or several amino acid residues may be substituted for the actual cleavage sequence and still elicit antibodies of the invention. Accordingly, the invention encompasses such functionally equivalent sequences.

The variable length peptide antigens may be in the form of the free amines (on the N-terminus) or acid-addition salts thereof. Common acid-addition salts are hydrohalic acid salts i.e., HBr, HI, or more preferably, HCl.

The amino acid residues of peptide antigens can be in their protected or unprotected form, as is otherwise understood to those of skill in the art. Also, appropriate amino, or carboxy protecting groups can be used. It is also recognized that the peptide antigens may be extended at the N- or carboxy terminal region to include additional amino acid residues of the cleavage site.

Amino acid sequences of cleavage sites are available for many precursor proteins. Peptide antigens corresponding to these sites can be synthesized according to the aforementioned techniques. Examples of such precursor proteins include, but are not limited to, Factor VIII, Protein C (Foster et al., *PNAS USA* 82:4673 (1985)); Factor IX (Yoshitake et al., *Biochemistry* 24:3736 (1985)); Factor X (McMullen et al., *Biochemistry* 22:2875 (1983)); Prothrombin (Degen et al., *Biochemistry* 2:2087 (1985)); and Factor VIII (Vehar et al., *Nature* 312:337 (1984)).

If the amino acid sequence of a cleavage site is unavailable it can be obtained by standard amino acid sequencing techniques well known to those of skill in the art (Edman, P. et al., *Eur. J. Biochem.* 1:80–91 (1967)). If the site of cleavage is not known it can be determined by comparing the amino acid sequence of the precursor protein with its cleavage products, particularly mature proteins. The cleavage site may also be reduced from the cDNA sequence of a protein by knowing the cleavage specificities of the activating enzyme. Once obtained, peptide antigens corresponding to these sites can be synthesized according to the aforementioned techniques.

The peptide antigens of the invention can be used to elicit antibody-inhibitor compositions of the invention using the techniques of sensitization and/or immunization, cell fusion, ascites production, selection of mixed hybridomas, or subcloning of monoclonal hybridomas. These techniques are generally well known in the art. Attention, for example, is brought to Koprowski, et al., U.S. Pat. No. 4,172,124, Koprowski, et al., U.S. Pat. No. 4,196,265, Wands et al., U.S. Pat. No. 4,271,145, or Douillard, J. Y. and Hoffman, T., *Basic Facts about Hybridomas, in Compendium of Immunology*, Vol. II, L. Schwartz, ed. (1981), which are herein incorporated by reference.

In general, the purified epitopic peptides have attached at the C- or N-terminus a cysteine, to permit unidirectional attachment of the peptide antigen to an immunogenic protein through a connecting bridge, e.g., maleimidobenzoylated (MB)-keyhole limpet hemocyanin (KLH). Other immunogenic conjugates can also be used, e.g., albumin, and the like. In addition, the peptide antigens may be coupled to other carrier proteins by other conjugation techniques such as glutaraldehyde, carbodiimide bis-diazotized benzamidine, etc. (Harlow, E. and Lane D., *Antibodies, A Laboratory Manual*, Cold Spring Harbor Laboratory (1988)). The resulting structure may have several peptide structures linked to one molecule of protein.

Lines of somatic cells immunized against the peptide antigens of the invention can be obtained by any suitable immunization technique. The host is sensitized by administering the antigen, usually in the form of a protein conjugate, as hereinbefore indicated, by any suitable method, preferably by injection, either intraperitoneally, intravenously, subcutaneously, or by intra-foot pad. Adjuvants may be included in the immunization protocol. Virus, bacteria or other cells may also be employed.

The initial immunization with the protein bound antigen can be followed by several booster injections given periodically at intervals of several weeks. Immunized somatic cells are then obtained periodically from the host by procedures well known to those skilled in the art. The antibody contained in the plasma of each host can then be tested for its specificity to the target precursor protein. The host having the highest anti-precursor protein response is usually most desirable as the donor of the antibody secreting somatic cells. Hyperimmunization can be effected by repeatedly injecting the additional amounts of peptide-protein conjugate by an intravenous and/or intraperitoneal route.

The immunized somatic cells, preferably spleen cells, must then be fused with another cell line to produce hybridomas capable of secreting anti-precursor protein specific antibodies which are capable of inhibiting precursor protein activity. Some of the factors to be considered in the selection of another cell line for fusion are rapid, uniform growth characteristics, metabolic deficiency for growth in a specified component of the growth medium, and potential for good fusion frequency. Malignant cells have been found to be particularly suitable for fusion. The species from which such cell lines are derived is also an important factor. Several cell lines including mouse, rat, hamster and human myeloma lines are available and are preferred for obtaining hybridomas. A variety of fusing agents may be employed to induce cell fusion. Polyethylene glycol and virus-induced fusions are particularly efficacious and are the preferred agents.

Preferred conditions for the somatic cell fusion and establishment of the hybridoma cell lines are those reported by Kohler and Milstein, *Nature* (London) 256:496 (1975), which is herein incorporated by reference.

Preferred hosts for the production of somatic cells are mouse, in particular BALB/c, or AJ. Particularly suited malignant cells for the purpose of establishing hybridoma cell lines by somatic cell fusion are myeloma cell lines, in particular the Sp2/0 and NS-1 lines.

Rapid identification of suitable hybrids is a key procedure in all hybridoma work. Early detection of hybridoma antibodies may be performed by any suitable assay; particularly preferred are radioimmunoassays, enzyme-immunoassays, and the like.

Maintenance of the hybridomas is accomplished by the use of appropriate selection growth medium. Standard tissue culture medium together with feeder cells are usually preferred. Hybrids may also be grown in horse or calf serum or in serum-free media, and the like.

Hybrids obtained by fusion are heterogenous colonies. In order to get a homogeneous line expressing a given function, these colonies are preferably cloned. By cloning is meant the process of achieving growth of a cell line from a single parental cell, viz., a monoclonal expansion. Such cloning may be achieved by any suitable technique, such as by agarose technique and the like.

Antibody secreting hybrids grown in tissue culture flasks yield supernatants with variable concentrations of antibody, usually in the range of about 1–30 ug/ml. Higher yields are, therefore, obtained preferably by transferring hybrids into animals with inflammatory ascites. Ascites are preferably induced by intraperitoneal injection of the hybridoma or by other suitable methods.

Preservation of the hybridoma important and may be accomplished by any suitable technique. A preferred method is by subcloning or by freezing adequate amounts of the hybridoma early after fusion, and to reclone the cell population, as needed.

The term "hybridoma," as used herein, refers to hybrid cells obtained by the technique of somatic cell fusion, as described in the specification, the hybrid so obtained having the capability of producing anti-factor XIII antibodies capable of inhibiting Factor XIII activity.

The term "monoclonal antibodies," as used herein, refers to antibodies produced by a homogenous line of a cloned colony of cells, derived from a single parental hybridoma.

Besides the above identified method for obtaining monoclonal antibodies, there are other methods for producing antibodies or antibody fragments. It is recognized that any such method could be utilized to make the antibodies of the present invention. See, for example, Harlow and Lane, Antibodies: A Laboratory Manual, Cold Spring Harbor Laboratory, Cold Spring Harbor, N.Y. (1988); Davis et al., *Biotechnology* 9:165–169 (1991); Buchner and Rudolph, *BioTechnology* 9:157–162 (1991) and the references cited by these articles.

Once the monoclonal hybridoma has been prepared, it is a matter of routine experimentation in the art to isolate the desired antibodies from the supernatant. Well known techniques, such as salt precipitation, gel chromatography, ion exchange chromatography, affinity chromatography, and the like, can be used to obtain the antibodies in substantially pure form. By "substantially pure form," it is meant that the antibodies are essentially free from non-monoclonal antibody impurities, such as other proteins, other antibodies having different specificities, nucleic acids, polysaccharides, cell fragments, and the like. The antibodies can be used in soluble form or can be immobilized on an aqueous and soluble solid-phase, to obtain insolubilized antibodies.

The term "epitope," as used herein, refers to specific amino acid sequences characteristic of a protein, in which sequences arranged in a characteristic configuration can elicit antibodies which bind specifically to said sequences, in the configuration in which they appear. The antibodies which are elicited are not capable of binding to the same amino acids when they occur in a different configuration or order.

The antibodies, polyclonal or monoclonal, may be "humanized" (i.e., nonimmunogenic in a human) by recombinant or other technology. Humanized antibodies may be produced, for example, by replacing an immunogenic portion of an antibody with a corresponding, but nonimmunogenic portion. For a discussion of such chimeric antibodies, see, for example, Robinson et al., Publication PCT/US 86/02269: Akira et al. EPA 184,187; Taniguchi, M., EPA 171,496; Morrison et al., EPA 173,494; Neuberger et al., PCT WO 86/01533; Cabilly et al. EPA 125,023; Better et al., *Science* 240:1041–1043 (1988); Liu et al., *Proc. Natl. Acad. Sci. USA* 84:3439–3443 (1987); Wood et al., *Nature* 314:446–449; and Shaw et al., *J. Natl. Cancer Inst.* 80:1553–1559 (1988). General reviews of "humanized" chimeric antibodies are provided by Morrison, S. L., *Science* 229:1202–1207 (1985) and by Di et al., *BioTechniques* 4:214 (1986).

The antibody-inhibitors of the present invention, produced by the method of the present invention, can be utilized in any of a myriad of applications normally described for such antibodies. For example, these antibodies can be used in the development of a radioimmunoassay or enzyme-linked immunoassay for a precursor protein. They can also be used as immunoaffinity ligands for the purification of precursor proteins. In addition, they be used for the in vitro detection of a precursor protein or the activated protein species in clinical samples and the like.

There are many carriers to which the monoclonal antibodies of the invention can be bound and which can be used in detecting the presence of a precursor protein. Well-known carriers include glass, polystyrene, polypropylene, polyethylene, dextran, nylon, amylases, natural and modified celluloses, polyacrylamides, agaroses, and magnetite. The nature of the carrier can be either soluble to some extent or insoluble for purposes of the invention. Those skilled in the art will know many other suitable carriers for binding monoclonal antibodies or will be able to ascertain such, using routine experimentation.

The term "antibodies" as used in this invention is meant to include intact molecules as well as fragments thereof, such as for example, Fab, Fv, F(ab)$_2$, which are capable of binding antigen.

There are many different labels and methods of labeling known to those of ordinary skill in the art. Examples of the types of labels which can be used in the present invention include enzymes, radioisotopes, fluorescent compounds, chemiluminescent compounds, bioluminescent compounds, and metal chelates. Those of ordinary skill in the art will know of other suitable labels for binding to the monoclonal antibodies, or will be able to ascertain such, using routine experimentation. Furthermore, the binding of these labels to the monoclonal antibodies can be done using the standard techniques common to those of ordinary skill in the art.

One of the ways in which a monoclonal antibody of the invention can be detectably labeled is by linking the monoclonal antibody to an enzyme. This enzyme, in turn, when later exposed to its substrate, will react with the substrate in such a manner as to produce a chemical moiety which can be detected as, for example, by spectrophotometric or fluorometric means. Examples of enzymes which can be used to detectably label are malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

The presence of the detectably labeled monoclonal antibody can also be detected by labeling the monoclonal antibody with a radioactive isotope. The presence of the radioactive isotope can then be determined by such means as the use of a gamma counter or a scintillation counter. Isotopes which are particularly useful are $^3$H, $^{125}$I, $^{131}$I, $^{32}$P, $^{35}$S, $^{14}$C, $^{51}$Cr, $^{36}$Cl, $^{57}$Co, $^{58}$Co, $^{59}$Fe, and $^{75}$Se.

It is also possible to detect the binding of detectably labeled monoclonal antibodies by labeling the monoclonal antibody with a fluorescent compound. When the fluorescently labeled monoclonal antibody is exposed to light of the proper wavelength, its presence can then be detected due to the fluorescence of the dye. Among the most commonly used fluorescent labeled compounds are fluorescein isothiocyanate, rhodamine, phycoerythrin, phycocyanin, allophycocyanin, o-phthalaldehyde, and fluorescamine.

The monoclonal antibodies of the invention can also be detectably labeled using fluorescence emitting metals such as, $^{152}$Eu, or others of the lanthanide series. These metals can be attached to the antibody molecule using such metal chelating groups as diethylenetriaminepentaacetic acid (DTPA) or ethylene diaminetetraacetic acid (EDTA).

Another way in which the monoclonal antibody can be detectably labeled is by coupling it to a chemiluminescent compound. The presence of the chemiluminescent-tagged monoclonal antibody is then determined by detecting the presence of luminescence that arises during the course of the chemical reaction. Examples of particularly useful chemiluminescent labeling compounds are luminol, isoluminol, aromatic acridinium ester, imidazole, acridinium salt, and oxalate ester.

Likewise, a bioluminescent compound may also be used to label the monoclonal antibody. Bioluminescence is a special type of chemiluminescence which is found in biological systems and in which a catalytic protein increases the efficiency of the chemiluminescent reaction. The presence of the bioluminescently labeled monoclonal antibody would be determined by detecting the presence of luminescence. Important bioluminescent compounds for purposes of labeling are luciferin, luciferase, and aequorin.

Another technique which may also result in greater sensitivity consists of coupling the antibodies to low molecular weight haptens: These haptens can then be specifically detected by means of a second reaction. It is common, for example, to use such haptens, as biotin (reacting with avidin) or dinitrophenol, pyridoxal, and fluorescamine (reacting with specific anti-hapten antibodies) in this manner.

The inhibitor compositions of the present invention in the form of antibodies or antibody fragments can also be formulated according to known methods to prepare pharmaceutically useful compositions, such as by admixture with a pharmaceutically acceptable carrier vehicle. Suitable vehicles and their formulation are described, for example, in Remington's Pharmaceutical Sciences (16th Ed., Osol, A. (ed.), Mack, Easton Pa. (1980)). In order to form a pharmaceutically acceptable composition suitable for effective administration, such compositions will contain an effective amount of the hapten-binding molecule or thrombolytic agent, either alone, or with a suitable amount of carrier vehicle.

Additional pharmaceutical methods may be employed to control the duration of action. Controlled release preparations may be achieved by the use of polymers to complex or absorb the antibody or antibody fragment-inhibitor compositions of the present invention. The controlled delivery may be exercised by selecting appropriate macromolecules (for example, polyesters, polyamino acids, polyvinyl pyrrolidone, ethylenevinylacetate, methylcellulose, carboxymethylcellulose, or protamine sulfate). The rate of drug release may also be controlled by altering the concentration of such macromolecules. Another possible method for controlling the duration of action comprises incorporating the therapeutic agents into particles of a polymeric substance such as polyesters, polyamino acids, hydrogels, poly(lactic acid) or ethylene vinylacetate copolymers. Alternatively, it is possible to entrap the therapeutic agents in microcapsules prepared, for example, by coacervation techniques or by interfacial polymerization, for example, by the use of hydroxymethylcellulose or gelatin-microcapsules or poly-(methylmethacrylate) microcapsules, respectively, or in a colloid drug delivery system, for example, liposomes, albumin microspheres, microemulsions, nanoparticles, nanocapsules, or in macroemulsions. Such teachings are disclosed in Remington's Pharmaceutical Sciences (1980).

It is contemplated that inhibitory compositions of the present invention will be administered to an individual in therapeutically effective amounts. That is, in an amount sufficient to inhibit the activation of the target protein. The effective amount of the inhibitory composition will vary according to the weight, sex, age, and medical history of the individual. Other factors which influence the effective amount may include, but are not limited to, the severity of the patient's condition, the concentration of the target protein to be inhibited in a particular individual or target tissue, the stability of the target protein and the inhibitory composition, the kinetics of interactions between the target protein and the inhibitory composition, the concentration of the activating enzyme, the presence of activating enzyme inhibitors, previous exposure to the inhibitory compound, kidney disease, etc. Generally, the inhibitory composition will be administered in doses ranging from about 15 to about 50 µg/ml/blood, more generally about 15 µg/ml/blood to about 30 µg/ml/blood.

The pharmaceutically prepared inhibitory compositions of the invention may be provided to a patient by means well known in the art. Such means of introduction include oral means, intranasal means, subcutaneous means, intramuscular means, intravenous means, intraarterial means, or parenteral means.

The inhibiting molecule of the present invention may be dissolved in any physiologically tolerated liquid in order to prepare an injectable bolus. It is preferable to prepare such a bolus by dissolving the molecule in normal saline.

As noted above, an antibody molecule of the present invention includes both monoclonal antibodies and fragments thereof. It may be preferable in some situations to employ the F(ab), F(ab')$_2$ or Fv fragment of such an antibody in order to minimize any immunological reaction caused by the Fc portion of the immunoglobulin.

Inhibitory compositions of the present invention in the form of monoclonal antibodies are ideally suited for the preparation of a kit. Such a kit may comprise a carrier means being compartmentalized to receive in close confinement one or more container means such as vials, tubes, and the like, each of said container means comprising the separate elements of the immunoassay or imaging method to be used. The types of immunoassays which can be incorporated in kit form are many. Typical examples of some of the immunoassays which can utilize the antibodies of the invention are competitive immunoassays and immunometric, or sandwich immunoassays.

The present invention is particularly drawn to inhibitory compositions which are useful in treating myocardial infarction and blood clots within a patient. Blood clots which may be treated according to the methods of the invention include, but are not limited to pulmonary thromboembolism, deep venous thrombosis, cerebral embolism, renal vein and peripheral arterial thrombosis, and the like. The compositions comprise inhibitors of coagulation factors, particularly inhibitors of Factor XIII. Monoclonal antibodies which are capable of inhibiting the activity of Factor XIII are especially useful as inhibitory compositions. More specifically, the antibodies are capable of inhibiting the crosslinking activity of Factor XIII A. Thus, the inhibitors and monoclonal antibodies of the present invention inhibit the formation of fibrin γ-dimers and encourage clot lysis.

Factor XIII inhibiting molecules encompass molecules which are capable of inhibiting Factor XIII activity, particularly antibodies, monoclonal antibodies and factors thereof. While it has been difficult to raise monoclonal antibodies which specifically bind to Factor XIII and inhibits its activity, the present invention provides a method for making such antibodies.

Peptides capable of raising antibodies specific for Factor XIII were synthesized. These peptides mimic the thrombin cleavage site of Factor XIII or a site close to the cleavage site.

Representative compounds of the invention useful for eliciting anti-Factor XIII antibodies (also of the invention) include those having the formula:

NH$_2$-G-V-N-L-Q-E-F-C-COR$^1$, (SEQ ID No: 1)

where

G is gly:

V is val;

N is asn;

L is leu;

Q is gln;

E is glu;

F is phe;

C is cys;

$R^1$ is $R^2$; -lys-CO-$R^2$; -lys-arg-CO-$R^2$; or -lys-arg-glu-CO-$R^2$;

$R^2$ is -cys-CO-$R^3$; OH; OM or $NR^4R^5$;

$R^3$ is OH; OM or $NR^4R^5$;

M is a pharmaceutically acceptable cation or a lower ($C_1$-$C_6$) branched or unbranched alkyl group:

$R^4$, $R^5$ are the same or different and selected from the group consisting of H or a lower alkyl group.

To obtain monoclonal antibodies to the amino-terminal or carboxy-terminal side of the thrombin cleavage site, any sequence of amino acids corresponding to that site can be utilized, e.g., $X_1$-P-R-G-V-N-E-Q-F-$X_2$ (SEQ ID No: 2); and the like, where $X_1$ denotes that the sequence can be extended with additional N terminal amino acids up to about 10 amino acids;

$X_2$ denotes that the sequence can be extended with other C-terminal amino acids up to about 10 amino acids;

P is proline:

R is arginine;

G is glycine;

V is valine;

N is asparagine;

E is glutamic acid;

Q is glutamine; and

F is phenylalanine.

Hybridomas producing anti-Factor XIII antibodies of the invention may be obtained using the peptide antigens described above by standard techniques described earlier. For identification of desired hybridomas, a radioimmunoassay utilizing Factor XIII coated microtiter wells exposed to the antibody, and then exposing the antigen antibody complex to radiolabelled anti-Fab fragment antibody is preferred (See, Klinman et al., *Ann. Immunol.* (Paris) 127C: 489 (1976), which is herein incorporated by reference).

The invention is also drawn to the use of the monoclonal antibody-inhibitors or antibody fragment-inhibitors of coagulation factors for treating myocardial infarction and blood clots within a patient. The method involves administering the monoclonal antibody or fragment thereof alone or in combination with a thrombolytic agent to a recipient patient. Such antibody fragments include, for example, F(ab), F(ab')$_2$, Fv or F(ab) molecules.

When administered alone the antibody-inhibitor of the invention enhances in vivo thrombolysis by significantly inhibiting fibrin-fibrin and $\alpha_2$-antiplasmin-fibrin crosslinking.

When used alone, an amount of the Factor XIII inhibiting molecule capable of inhibiting Factor XIII and thereby enhancing clot lysis when provided to a patient is a "therapeutically effective" amount. In order to enhance clot lysis and prevent clot reformation, it is desirable to provide between about 15 µg/ml to about 50 µg/ml of patient blood volume. This dosage may be administered, in one embodiment, over a period of between about 20 to about 240 minutes, by continual intravenous infusion. Alternatively, it is possible to provide the molecule in an intravenously injectable bolus at a dose of between about 15 µg to about 150 µg/ml/blood volume, and most preferably between about 15 to about 30 µg/ml of patient blood volume. If the molecule is provided in this manner, a single bolus is sufficient to prevent potential clot reformation.

Alternatively, the Factor XIII inhibiting molecule is administered with a thrombolytic agent. In this embodiment, the molecule and the thrombolytic agent of the present invention are intended to be co-administered to the recipient.

By the term "co-administration" it is intended that each of the Factor XIII inhibiting molecules, (antibody molecules or fragments thereof) and thrombolytic agent will be administered during a time frame wherein the respective periods of pharmacological activity overlap. While the two agents may be administered simultaneously or sequentially, it is preferable to administer them simultaneously.

The term "thrombolytic agent" is meant to refer to any agent capable of either dissolving a fibrin-platelet clot, or inhibiting the formation of such a clot. Examples of thrombolytic agents include streptokinase, prourokinase, urokinase, and tissue-type plasminogen activator. Use of t-PA for these purposes is especially preferred. Although natural t-PA may be employed, it is preferable to employ recombinant t-PA. The invention may additionally employ hybrids, physiologically active fragments, mutant or chimeric forms of the above thrombolytic agents including single chain urokinase plasminogen activator (scu-PA) and active fragments thereof. The term "tissue-type plasminogen activator" as used herein is intended to include such hybrids, fragments and mutants, as well as both naturally derived and recombinantly derived plasminogen activators.

When the Factor XIII inhibiting molecule is co-administered with a thrombolytic agent, it is desirable to provide about 15 µg/ml to about 150 µg/ml of patient blood volume. This dosage may be administered, in one embodiment, over a period of about 20 to about 240 minutes, by continuous intravenous infusion. Alternatively, it is possible to provide the antibody or fragment thereof in an intravenously injectable bolus at a dose of between about 15 µg to about 150 µg/ml/blood volume, and most preferably between about 15 to about 30 µg/ml of patient blood volume.

An amount of thrombolytic agent capable of causing such lysis is a "therapeutically effective" amount. The thrombolytic agent of the present invention is preferably provided at a dose of between about 0.5 to about 1.5 mg per kg of patient weight. In one embodiment, the thrombolytic agent is provided over a prolonged period (i.e., from about 180 to about 1440 minutes). In a preferred embodiment, the thrombolytic agent of the present invention is provided as an intravenously injected bolus containing between about 15 µg/ml to about 150 µg/ml blood volume, and most preferably between about 15 µg to about 30 µg/ml blood volume. The thrombolytic agent of the present invention may be dissolved in any physiologically tolerated liquid in order to prepare an injectable bolus. It is, however, preferable to prepare such a bolus by dissolving the thrombolytic agent in normal saline.

As would be apparent to one of ordinary skill in the art, the required dosage of the anti-Factor XIII antibody or thrombolytic agent will depend upon the severity of the condition of the patient, and upon such criteria as the patient's height, weight, sex, age, and medical history.

The antibody or fragment thereof of the present invention and thrombolytic agent can be formulated according to known methods to prepare pharmaceutically useful compositions as previously described.

The thrombolytic agent or antibody or fragment thereof may be provided to a patient by means well known in the art as described previously. In the most preferred method of treatment for myocardial infarction, a patient is provided with a bolus (intravenously injected) containing between about 15 µg/ml to about 30 µg/ml of patient blood volume.

Generally, the results reported herein demonstrate that an inhibitory composition, particularly a monoclonal antibody, can be used to neutralize the catalytic function of a precursor protein, particularly a coagulation enzyme. This approach can be applied to biological processes which are tightly governed by enzymes. Because coagulation is a finely balanced system in which the effects of thrombolytic enzymes (generally serine proteases) are pitted against the effects of other coagulation enzymes (like Factor XIII) pathological alterations in clotting can be treated by augmenting thrombolytic enzyme activity or by neutralizing coagulation enzymes.

It is recognized that the methods of the invention can be utilized to develop other antibodies, polyclonal and monoclonal, which specifically bind to the activated form of a protein and not to the zymogen or precursor protein. The invention therefore also relates to these antibodies or antibody fragments. For example, antibodies may be generated that will bind only to active Factor XIII. These antibodies do not cross-react or bind to the zymogens or precursor proteins previously described. The antibodies specific for active Factor XIII may be generated by the techniques set forth above. In particular, monoclonal antibody 394 was generated by the techniques set forth above using the peptide immunogen G-V-N-L-Q-E-F-C (SEQ ID No: 3). Such antibodies are useful for detecting or measuring the active enzyme in vitro or in vivo.

When the active form of Factor XIII-specific antibodies are in the monoclonal form, such detection means may be incorporated into a kit, as described above, and/or used in an immunoassay. Immunoassays generally include techniques that are based upon the formation of a complex between the antigenic substance being assayed and an antibody or antibodies in which one or the other member of the complex may be detectably labeled. With competitive immunoassay techniques, the antigenic substance in a sample fluid being tested competes with a known quantity of antibody binding sites. The amount of labeled antigen bound to the antibody is inversely proportional to the amount of antigen in a sample.

By contrast, most immunometric assays employ a labeled antibody. In such an assay, the amount of labeled antibody associated with the complex is directly proportional to the amount of antigenic substance in a fluid sample.

In sandwich immunometric assays, a quantity of unlabeled antibody is bound to a solid support which is insoluble in the fluid being tested. This immobilized antibody is first contacted with the sample being tested so that a binary antigen-antibody complex is formed. After a suitable incubation period, the solid support is washed to remove unbound antigens, then contacted with a solution containing a known quantity of a second antibody. After a second incubation period, the solid support is then washed a second time to remove the unreacted antibody. A labeled anti-antibody to the second antibody is then added, allowed to incubate for a sufficient amount of time, and the complex then washed. The washed solid support is then tested to detect and quantify the presence of labeled antibody, for example by measuring the emitted radiation of a radioactive label. The amount of labeled antibody detected is compared to that for a negative control sample. This type of assay is frequently referred to as a two-site or sandwich assay, since the antigen has two antibodies bonded to its surface at different locations. See David et al., U.S. Pat. No. 4,376,110.

Simultaneous and reverse assays may also be used to test for the presence of active Factor XIII. A simultaneous assay involves a single incubation step as the antibody bound to the solid support and the labeled antibody are both added to the sample being tested at the same time. After incubation, the solid support is washed to remove unbound analyte and unbound antibody, and the bound antibody-analyte-labeled antibody "sandwich" is detected as with a conventional "forward" sandwich assay. A reverse assay involves the stepwise addition first of a solution of labeled antibody to the fluid sample followed by the addition of unlabeled antibody bound to a solid support after a suitable incubation. After a second incubation, the solid phase is washed in conventional fashion and the amount of labeled complex is detected as before.

U.S. Pat. No. 4,279,885 to Reese et al. describes a solid phase competitive protein binding assay where an antigen or hapten can be assayed. The method involves competition between the analyte and a labeled form thereof for a limited number of receptor or binding sites which are immobilized to a solid support. The assay may be conducted by mixing the components simultaneously or sequentially. The sequential assay involves contacting a solution of an analyte with a support containing immobilized receptors or antibodies, followed by contacting the mixture with a tracer. The tracer may be the analyte, or analog thereof, which contains a label or tag.

In addition to the above-described competitive, immunometric, and sandwich assays, other variants of these assays exist, all of which are within the skill of the routineer.

Having now generally described this invention, the same will be better understood by reference to certain specific examples which are included herein for purposes of illustration only, and are not intended to be limiting of the invention, unless specified.

EXPERIMENTAL

Materials

Materials were obtained from the following suppliers: Factor XIII-free fibrinogen, human Factor XIII (American Diagnostica, Greenwich, Conn.); affinity purified goat anti-(mouse Fab') (GAMFab), Cappel Laboratories (Malvern, Pa.); high and low molecular weight protein standards, Pharmacia (Uppsala, Sweden); pre-stained protein standards, (Bio-Rad, Richmond, Calif.); BALB/C mice (Charles River, Wilmington, Mass.); bovine thrombin, Parke-Davis (Morris Plains, N.J.); Freund's adjuvant (Difco, Detroit, Mich.); keyhole limpet hemocyanin, D-phenylalanyl-L-prolyl-L-arginine chloromethyl ketone /PPACK/ (Calbiochem, La Jolla, Calif.), polyvinylidene difluoride transfer membranes (Millipore, Bedford, Mass.); iodoacetamide, RIA-grade bovine serum albumin, protein A, N,N'-Dimetyl casein (Sigma, St. Louis, Mo.); human tissue plasminogen activator (Genentech, South San Francisco, Calif.); placental Factor XIII, rabbit antiserum against A-subunit of Factor XIII (Dignostika Stago, France via American Diagnostika, Parrsipany, N.J.). All other chemicals were of reagent grade or better. Fresh frozen plasma was obtained from random donors to Mass. General Hospital, Boston, Mass.

Methods

Monoclonal Antibody Production

To produce antibody to the thrombin activation site of Factor XIII, a peptide was synthesized which mimics the amino acid sequence of the amino terminus of thrombin-activated A-subunit of Factor XIII. This thrombin cleavage site (TCS) peptide had the sequence $NH_2$-G-V-N-L-Q-E-F-C-COOH (SEQ ID No: 3) which duplicates the A-subunit amino acid sequence of residues 38–44. The carboxy terminal cysteine is not part of the A-subunit sequence and was added to the peptide for the purpose of chemical coupling. The peptide was manually synthesized using a modified Merrifield method as we have previously described (Ridge et al., *Chemical Synthesis of Peptides*; In Fozzard et al., *The Heart and the Cardiovascular System* (Eds.), Raven Press, New York (1986). For the purpose of immunization, the peptide was chemically coupled to keyhole limpet hemocyanin (KLH) by the heterobifunctional crosslinking agent bromoacetic acid N-hydroxy-succinimide ester. The amino acid sequence of the peptide and its chemical coupling to LKH were verified by amino acid analysis on a Waters Picotag system. After coupling the free peptide was separated from the KLH-peptide conjugate by extensive dialysis.

CAF mice were immunized subcutaneously with 15 μg of KLH-peptide conjugate which was emulsified in complete Freund's adjuvant 1 month later and then every three months until somatic cell fusion. Prior to somatic cell fusion the antibody titer to the peptide was determined in a solid-phase radioimmunoassay. The TCS peptide was added to the wells of a polyvinylchloride plate (10 μgs/ml, 25 μl per well). After 1–2 hours the peptide was washed off and the non-specific binding sites were blocked with 1% bovine serum albumin (BSA) for 1 hour. Ten-fold serial dilutions of the mouse antiserum (25 μl) were added to each well and incubated for 1 hour at room temperature. The wells were again washed and 25 μl of goat anti(mouse Fab'2) (GAM) was added and allowed to incubate for 1 hour. The GAM was removed and the plates were washed. The amount of bound antibody was counted in a γ-scintillation counter. Cells from the mouse with the highest antibody titer was used for somatic cell fusion which was performed according to the method described by Galfre and colleagues (Galfre et al., *Scand. J. Haemat.* 19:443–448 (1977)). Hybridomas secreting peptide specific antibody were selected using a reverse solid-phase radioimmunoassay with GAM as described by Eshhar (Eshhar, Z. *Hybridoma Technology in the Biosciences and Medicine* (ed.):3–41 (1985)). Hybridomas producing anti-TCS peptide antibody were then screened for their binding to purified Factor XIII in a solid-phase RIA using radiolabelled GAM (see above). From these assays monoclonal antibody (MAb) 309 was selected for further characterization.

Specificity Assays

To determine the binding specificity of the antibody, a peptide was synthesized that contains the sequence $NH_2$-P-R-G-V-N-L-Q-E-F-C-COOH (SEQ ID No: 4), which mimics the structure of the A-subunit of Factor XIII zymogen except for the carboxy terminal cysteine residue. This peptide was identical to the TCS peptide except for the presence of two more $NH_2$ terminal amino acids which are present in the zymogen and not in the activated Factor XIII. Therefore, this peptide spans the thrombin cleavage site. The peptide was synthesized on a Milligen 9050 peptide synthesizer using F-moc chemistry. The peptide was determined to be homogenous by high performance liquid chromatography studies on a Waters 441 system. The peptide composition was confirmed by amino acid analysis on a Waters Picotag system.

To ascertain whether MAb 309 was able to bind specifically to thrombin cleaved Factor XIII we compared the binding of the MAb to the TCS peptide with the binding of the MAb to the spanning peptide in a radioimmunoassay. Wells of a microtiter plate were coated with the TCS peptide (25 μl of a 50 μg/mL solution) for 1–2 hours. Nonspecific protein binding sites were blocked with 1% BSA for 1 hour. After washing, spent hybridoma supernatants were diluted serially in culture media and added to separate wells to incubate for 1 hour. The wells were then washed and incubated with 125I-GAMFAb (approximately 50,000 cpm) for an hour. The wells were again washed extensively, followed by counting in a γ scintillation counter to detect antibody binding.

The dilution of hybridoma supernatant which yielded about half of maximal binding was determined and subsequently used for inhibition studies. In these experiments, increasing amounts of soluble TCS peptide or spanning peptide were mixed with MAb 309 hybridoma supernatant and added to the TCS peptide-coated microtiter wells to inhibit the binding of the antibody. After incubation for 2 hours at room temperature, the wells were washed and the bound antibody was detected with $^{125}$I-GAMFAb as above. The percent of inhibition was computed as the fraction of binding in the presence of inhibitor compared to the binding in the absence of any inhibitor.

Avidity Measurements

To determine the avidity of MAb 309 for the TCS-peptide, avidity experiments were performed. The TCS-peptide was coupled to BSA using the heterobifunctional reagent bromoacetic acid N-hydroxy-succinimide ester as described above. After extensive dialysis to remove the uncoupled peptide, amino acid analysis was performed. The analysis demonstrated that 2.3 moles of TCS-peptide was coupled per mole of BSA. The BSA-peptide conjugate was then radiolabeled by the chloramine-T method (Greenwood et al. *Biochem. J.* 89:114–123 (1963)). The iodinated protein was separated from free iodide on a PD-10 column. The specific radioactivity was determined in triplicate by paper chromatography in 50% ethanol:water. Equilibrium saturation binding assays were performed to determine the MAb's avidity. In these assays MAb hybridoma supernatants were diluted in culture media to an antibody concentration below the expected Kd. The radiolabelled ligand was diluted in HEPES-buffered saline with 0.02% azide (HBSA) to concentrations approximately 10-fold above and below the Kd. The 100 μl of the diluted antibody was mixed with 100 μl of various concentrations of radiolabelled ligand and 100 μl of HBSA in test tubes. The tubes were incubated at 4° C. overnight. The 50 μl of goat antimouse antibody coupled to magnetic particles was added to each tube and allowed to incubate for 90 minutes at 4° C. Then 2 ml of ice-cold HBSA was added to each tube and the bound radiolabelled ligand was separated from the free ligan by centrifugation at 3000 rpm for 15 minutes at 4°. The initial estimate of background was obtained by performing the same experiment in parallel with a control MAb (anti-digoxin 40–160) of the same isotype. The avidity was calculated using the Ligan program on a Zenith microcomputer.

Purification of MAb 309

Culture supernatants were collected and MAb 309 was purified on Protein A-SEPHAROSE (beaded agarose) column. Culture supernatants were mixed with 1.5M Glycine in 3M NaCl, pH 8.9 (ratio 1:1) and incubated on column for a hour. Antibody was eluted from the column with 0.1M Na Citrate, pH 3.5, neutralized with 1M Tris HCl, pH 9.1 and concentrated.

Binding of MAb 309 to Purified Factor XIII

Plates were coated with 25 μl of placental Factor XIII ($A_2$) or plasma Factor XIII ($A_2B_2$) at a concentration 20 μg/ml. Culture supernatants with MAb 309 were incubated with antigen after blocking. The 50,000 cpm/well of $^{125}$I-GAM-FAb were added and residual radioactivity was measured on γ scintillation counter.

Assay for Transglutaminase Activity

Human Factor XIII A-Subunit activity was measured by the incorporation of 14C- putresceine into bovine α-casein using a filter paper assay as described by Lorand (Lorand et al. *Anal. Biochem.* 50:623–631 (1972)) with the following minor modifications. Fresh frozen human plasma, from at least 4 random donors was used as the source of Factor XIII. After heat inactivation of fibrinogen, Factor XIII was activated by a 30-minute incubation with 0.08 U of thrombin, 3.5 mM CaCl and 0.2M DTT (final concentrations) at 37° C. To determine the relative effect of MAb on Factor XIII activation. MAb 309 or a control MAb (anti-digoxin 40–160) at a final concentration of 1 mg/ml, were added before or after the activation of Factor XIII by thrombin. To terminate thrombin activation of Factor XIII. D-phenylalanyl-L-proyl-arginine-chloromethyl-ketone (PPACK) was added in a final concentration of $10^{-6}$M. Following the activation of Factor XIII by thrombin, Factor XIII transglutaminase activity was measured by the incorporation of $^{14}$C- putrescine into casein as described. After 30 minutes of incubation, iodoacetamide (100 µg/ml final concentration) was added to stop the reaction and 20 µl of each sample as spotted onto Whatman filter paper and counted in a scintillation counter.

Effect of MAb 309 on γ—γ Cross-Linking of Fibrinogen by Factor XIIIa

5 µl of placental Factor XIII (0.03 µg/ml) was preincubated with 25 µl of MAb 309 (2 mg/ml). After 30 minutes 5 λ of thrombin (0.01 U) and 5 µl of 10 mM CaCl$_2$ were added and incubated for 20 minutes at 37° C. Then Factor XIII-free fibrinogen (10 µg) was added and incubated for different times. Fibrin crosslinking was stopped by adding 10 µl of 9M Urea followed by immediately boiling the samples. The samples were then analyzed by SDS-PAGE on 7.5% gels under reducing conditions. Gels were stained by Coomassie Brilliant Blue and dried.

Clot Lysis Assay

Fresh frozen plasma was mixed with trace amounts of $^{125}$I-fibrinogen, about 20,000 cpm Plasma (25 µl) was incubated with 25 µl of MAb 309 or with a control (Tris-buffered saline with 0.02% azide) for 30 minutes before clotting with 25 µl of 20 mM CaCl$_2$. After 30 minutes the clotting was stopped with iodoacetamide (20 µl of 1 mg/ml solution). Human tissue plasminogen activator (5 U) was added to the clot in each tube. At 30 and 60 minutes, a 200 µl aliquot of supernatant was sampled and counted in a γ-scintillation counter to determine the percentage clot lysis. The percentage of clot lysis was computed as the quotient of the radioactivity released into supernatant as fibrin-degradation products divided by the initial radioactivity incorporated into the clot.

Factor XIII Activation by Thrombin and Calcium, Western Blotting

5 µl of purified plasma Factor XIII (0.5 µg) was preincubated with 15 µl of MAb 309 (or anti-digoxin MAb as a control) (2 mg/ml) for 30 minutes. The Factor XIII was activated by 10 µl of 0.02 IU of thrombin (in 15 mM CaCl$_2$) for 9, 5, 10, 15, 20 and 25 minutes at 37° C. Reactions were stopped immediately by adding 10 µl of sample buffer and boiling. Prepared samples were electrophoresed on 6% unreduced gels and electrophoretically transferred by semi-dry technique to PVDF-nitrocellulose paper. The membranes were washed in 0.3% Tween-TBS and blocked with 1% BSA-TBSA buffer.

In some experiments the nitrocellulose blots were probed with rabbit antisera against the a subunit of human Factor XIII (diluted 1:100) as a primary antibody, and $^{125}$I-protein A ($1.5 \times 10^6$ cpm) as a detecting agent. In other experiments the nitrocellulose blots were probed with a monoclonal antibody against the amino terminus of Factor XIII which is cleaved off during thrombin activation. In these experiments $^{125}$I-GAMFab ($1.5 \times 10^6$ cpm) was used to detect the bound primary antibody. After washing and drying, the nitrocellulose membrane was autoradiographed. In addition, when the monoclonal antibody to the N-terminal peptide of Factor XIII was used, the nitrocellulose blots were cut in even strips and the amount of bound radioactivity measured by γ-scintillation counting.

Results

Binding Specificity of MAb 309

From the somatic cell fusion of splenocytes from one immunized mouse, 30 hybridomas were considered to produce antibody to the TCS-peptide. Based upon its apparent avidity for the TCS-peptide, and its binding to Factor XIII in a solid phase assay, MAb 309 was selected for further study. Compared to a control antibody, MAb 309 bound to Factor XIII in a concentration dependent fashion.

To further characterize the binding specificity of MAb 309 we performed radioimmunoassays with the TCS-peptide and a peptide that spans the thrombin cleavage site (spanning peptide). Wells of a microtiter plate were coated with the TCS peptide. Then MAb 309 culture supernatants, diluted to give approximately 50% binding, were mixed with various concentrations of the TCS or spanning peptide and added to the microtiter plate wells. After 1 hour of incubation the wells were washed and $^{125}$I-GAM was added to detect the bound antibody. Both peptides inhibited the binding of MAb 309 in a parallel fashion at equivalent concentrations. This indicates that MAb 309 for the most part recognizes the amino acids distal, or C-terminal, to the thrombin cleavage site and does not require a free glycine amide for binding. Further, the results indicate that based on sequence alone. MAb 309 probably binds equally well to both activated Factor XIII and the zymogen.

To test the binding specificity of MAb 309 to Factor XIII compared to other proteins, an immunoblotting experiment using whole human platelets was performed. In this experiment, pooled human platelets were isolated from platelet-rich plasma by differential centrifugation and washing. The platelets were then mixed with SDS and reducing agent and run on polyacrylamide gels. After electrophoretic transfer to PVDF-nitrocellulose, immunoblotting was performed using MAb 309 as a probe. The immunoblots showed that MAb 309 binds to a single band of ~75,000 Mr, which corresponds to the Factor XIII A chain monomer. These experiments using purified plasma Factor XIII and solubilized, electrophoresed human platelets confirm the binding specificity of MAb 309 for Factor XIII A chain.

Binding Avidity of MAb 309

To estimate the binding affinity of MAb 309 we performed equilibrium saturation binding experiments with the TCS-peptide. The peptide binding avidity was chosen as an estimate of the Factor XIII binding avidity to obviate the potential difficulties of incomplete thrombin cleavage of Factor XIII, possible second site thrombin cleavage, molar excess of B chain, etc., that could confound estimates of the binding avidity of the antibody for Factor XIII. In these experiments, MAb 309 was diluted to achieve a concentration below the Kd. The antibody was then incubated with increasing concentrations of the ligand overnight at 4° C. Following washing with cold buffer, the ligand which was bound to MAb 309 was separated from the free ligand by binding with polyclonal goat antimouse antibodies. The binding experiments were then subject to nonlinear-least squares analysis using the LIGAND program. In these experiments, MAb 309 was found to have an avidity of $1.75 \pm 0.35 \times 10^9 M^{-1}$.

Effects of MAb 309 on Factor XIII Transglutaminase Activity in Plasma

Because MAb 309 bound to Factor XIII zymogen at the thrombin activation site, it was hypothesized that it might inhibit the activation of Factor XIII by thrombin. To test this, we measured Factor XIII activity in plasma samples using a modification of the assay originally described by Lorand. In this assay MAb 309 and a control antibody were compared for their effects on the Factor XIII catalysis of $^{14}$C-putrescine into casein. When Factor XIII was preincubated with MAb 309, it inhibited 99% of the Factor XIII activity. Fab 309 also inhibited cleavage of Factor XIII by thrombin excluding the possibility of immunoprecipitation of Factor XIII by complete MAb 309. Different thrombin inhibitors (PPACK, TLCK) in variable concentrations did not show significant differences in results.

Effects of MAb 309 on Clot Lysis

The most important natural substrate for plasma Factor XIII is fibrinogen. It is also known that in the presence of fibrinogen, the activation of Factor XIII proceeds differently. Similarly the binding of Factor XIII to fibrinogen may inhibit the binding of the MAb to the thrombin cleavage site. To determine the effects of the antibody on the physiologic Factor XIII activity during clotting we analyzed clots formed in the presence of MAb 309 or a control antibody. Incubation of placental Factor XIII with thrombin and calcium followed by the addition of Factor XIII fibrinogen caused γ—γ cross-linking in control samples. However, preincubation of Factor XIII with MAb 309 prevented formation of the γ—γ dimers of fibrin. Thus. MAb 309 inhibited the catalytic activity of Factor XIII with both small and large (fibrin) substrates.

The previous experiment demonstrated that MAb 309 inhibits Factor XIII using purified reagents. To investigate its effect in plasma, the effect of the MAb on clot lysis was studied. Clot lysis rates have been shown to depend on the amount of fibrin γ—γ chain and α—α cross-linking. In these assay MAb 309 or no antibody was added to plasma which had been mixed with radiolabelled fibrinogen. The plasma was then clotted by recalcification for 30 minutes at 37° C. Then tissue plasminogen activator (5 IU) was added to each tube and the amount of clot lysis was determined as a function of time. Clots having MAb showed 83% lypis as compared to 51% for controls without MAb 309, 30 minutes after adding tPA. Further after 60 minutes of tPA, clot samples with MAb 309 showed 91% lysis as compared with 71% for controls.

Monoclonal Antibody 309 Inhibits Thrombin Cleavage of Factor XIII

Monoclonal antibody 309 was derived in part to inhibit the thrombin activation of Factor XIII. To establish that this was its mechanism of inhibition, we studied the effect of MAb 309 or a control antibody on the rate of thrombin cleavage of Factor XIII. Factor XIII was activated for various lengths of time in the presence of MAb 309 or a control. Activated Factor XIII was detected by the shift in migration of the Factor XIII after activation (i.e.. MW decrease from 85,000 to 81,000, on immunoblots. After 10, 15, and 20 minutes of thrombin and calcium treatment Factor XIII ($A_2B_2$) was activated in controls (with anti-digoxin MAb), while $A_2B_2$ was not activated with MAb 309. Thrombin cut the 4 kDa peptide in the process of activation of Factor XIII in controls while with MAb 309 the A chain has been unchanged after 5, 10, 15, and 20 minutes of thrombin and calcium effect. MAb 309 inhibited the activation of Factor XIII, and protected release of the activation peptide from $A_2B_2$, respectively.

Discussion Relating to MAb 309

MAb 309 has been developed against a peptide that mimics the thrombin-activation sequence of the Factor XIII A-subunit. To establish its functional effect on Factor XIII and its activated form Factor XIIIa, MAb 309 was tested in a Factor XIII assay with small substrates (Lorand Assay), and with its natural substrate fibrin.

Thrombin activation of plasma Factor XIII was inhibited 99% when preincubated with MAb 309. MAb 309 prevented Factor XIII activation by inhibiting thrombin cleavage or the 4 kDa peptide which activates the zymogen. As a result MAb 309 inhibited the formation of fibrin γ-dimers in the process of plasma clotting and it accelerated lysis of plasma clots.

Lorand et al. *In Progress in Haematostasis and Thrombosis* 5:245–290 (1980) classified 3 types of acquired inhibitors of Factor XIII. Type I inhibitors interfere selectively with the conversion of Factor XIII to Factor XIIIa without inhibiting the transamidase activity. Type II inhibitors bind to fibrin and prevent fibrin from reacting properly with Factor XIIIa and type III inhibitors affect the fibrin-stabilizing activity of Factor XIIIa. Monoclonal antibody 309 belongs to type I inhibitors.

The present disclosure represents the first report of a monoclonal antibody against the A chain of Factor XIII which inhibits thrombin cleavage of Factor XIII. There is a need for such an inhibitor in thrombolytic therapy. The Factor XIII inhibitors further serve as prototypes for the generation or inhibitors of other coagulation factors and, more generally, inhibitors of any precursor protein.

Antibodies Specific to Active Factor XIII

In order to make a representative monoclonal antibody that will only bind to the activated form of Factor XIII, and not a Factor XIII zymogen, MAb 394 was generated using the gene peptide immunogen previously described (G-V-N-L-Q-E-F-C) (SEQ ID No: 3). The selection strategy employed generated MAbs that only bound to active Factor XIII, not its precursor zymogen. These MAbs bind with high avidity ($2.3 \pm 0.4 \times 10^9 M^{-1}$) to the activation peptide (G-V-N-L-R-E-F-C) (SEQ ID No: 5) that represents the "new" amino terminus of thrombin-cleaved Factor XIII. These same MAbs will not bind to a peptide representative of the sequence of Factor XIII zymogen (P-R-G-V-N-L-Q-E-F-C) (SEQ ID No: 4) as shown for a representative MAb in FIG. 1. These MAbs will not bind to Factor XIII zymogen but do bind to the thrombin-cleaved protein. The exquisite binding specificities of these MAbs make them useful reagents for detecting activated Factor XIII both in vitro and in vivo.

Deposits

MAb 309 was deposited on Mar. 11, 1991, at the ATCC 12301 Parklawn Drive, Rockville, Md., USA 20852. This deposit has been converted to comply with the requirements of the Budapest Treaty. MAb 309 has been given ATCC Designation number HB 10702.

MAb 394 was deposited in compliance with the Budapest Treaty on Mar. 6, 1992, at the ATCC 12301 Parklawn Drive, Rockville, Md. USA. 20852. MAb 394 has been given ATCC Designation number HB 10981.

Modifications of the above-described modes for carrying out the invention that are obvious to persons of skill in medicine, immunology, hybridoma technology, pharmacology, and/or related fields are intended to be within the scope of the following claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims. Also, many applications exist for this invention, some of which have been described. Other applications will be readily apparent to those of skill in the art.

What is claimed is:

1. A method for inhibiting the activation or active form of Factor XIII as a means of treating a patient with myocardial infarction or blood clots, said method comprising administering a therapeutically effective amount of an anti-Factor XIII antibody that binds the A subunit of Factor XIII at the thrombin cleavage site such that the ability of Factor XIII to catalyze the formation of γ—γ dimers of fibrin or the cross-linking of $\alpha_2$-antiplasmin to fibrin is inhibited.

2. The method of claim 1 wherein said antibody is a monoclonal antibody.

3. The method of claim 2, wherein said monoclonal antibody has specificity for a synthetic peptide which mimics the cleavage site of Factor XIII which is cleaved by thrombin during activation, said peptide having the following sequence:

$NH_2$-G-V-N-L-Q-E-F-C-COR$^1$     (SEQ ID No: 1)

where

G is gly; V is val; N is asn; L is leu; Q is gln; E is glu; F is phe; C is cys; and $R^1$ is one of $R^2$; -lys-arg-CO-$R^2$; or -lys-arg-glu-CO-$R^2$; or -lys-arg-glu-CO-$R^2$;

$R^2$ is -cys-CO-$R^3$; OH; OM or $NR^4R^5$;

$R^3$ is OH; OM or $NR^4R^5$;

M is a pharmaceutically acceptable cation or a lower ($C_1$-$C_6$) branched or unbranched alkyl group; and $R^4$, $R^5$ are the same or different and selected from the group consisting of H or a lower alkyl group.

4. A method for inhibiting the activation, or active form, of Factor XIII as a means of treating a patient having myocardial infarction or blood clots, comprising:

administering a therapeutically effective amount of a monoclonal antibody having specificity for a synthetic peptide which mimics the amino acid sequence on the amino-terminal side of the cleavage site of Factor XIII, said peptide having the following sequence:

$X_1$-P-R-G-V-N-E-Q-F-$X_2$     (SEQ ID No: 2)

where $X_1$ denotes that the sequence can be extended with additional N terminal amino acids up to about 10 amino acids, or otherwise denotes the N-terminus;

$X_2$ denotes that the sequence can be extended with other C-terminal amino acids up to about 10 amino acids, or otherwise denotes the C-terminus;

P is pro;

R is arg;

G is gly;

V is val;

N is asp;

E is glutamic acid;

Q is glutamine; and

F is phe.

5. The method of any of claims 1, 2, 3 or 4, wherein said method further comprises co-administering a therapeutically effective amount of a thrombolytic agent.

6. A kit useful for carrying out a method of treating a patient having myocardial infarction or blood clots, being compartmentalized in close confinement to receive two or more container means therein, which comprises:

(1) a first container containing a therapeutically effective amount of a Factor XIII inhibiting molecule that binds the A subunit of Factor XIII at the thrombin cleavage site such that the ability of Factor XIII to catalyze the formation of γ—γ dimers of fibrin or the cross-linking of $\alpha_2$-antiplasmin to fibrin is inhibited and wherein said Factor XIII inhibiting molecule is selected from the group consisting of monoclonal antibodies, fragments of monoclonal antibodies, single chain antibodies and humanized antibodies; and (2) a second container containing a therapeutically effective amount of a thrombolytic agent.

7. The kit of claim 6, wherein said Factor XIII inhibiting molecule is an anti-Factor XIII monoclonal antibody.

8. The kit of claim 7, wherein said monoclonal antibody is monoclonal antibody 309, deposited as ATCC Designation number HB 10702.

* * * * *